United States Patent [19]
Deeg et al.

[11] 4,079,470
[45] Mar. 21, 1978

[54] ARTIFICIAL INTRAOCULAR LENS

[75] Inventors: Emil W. Deeg; David A. La Marre, both of Woodstock, Conn.

[73] Assignee: American Optical Corporation, Southbridge, Mass.

[21] Appl. No.: 769,073

[22] Filed: Feb. 16, 1977

[51] Int. Cl.$^2$ .............................................. A61F 1/16
[52] U.S. Cl. ......................................... 3/13; 351/159; 351/167
[58] Field of Search ................. 3/13, 1; 351/159, 160, 351/167

[56] References Cited

U.S. PATENT DOCUMENTS

| | | | |
|---|---|---|---|
| 3,673,616 | 7/1972 | Fedorov et al. | 3/13 |
| 3,925,825 | 12/1975 | Richards et al. | 3/13 |
| 3,971,073 | 7/1976 | Richards et al. | 3/13 |
| 3,996,627 | 12/1976 | Deeg et al. | 3/13 |

OTHER PUBLICATIONS

"A weightless Iseikonic Intraocular Lens" by R. D. Binkhorst et al., American Journal of Ophthalmology, vol. 58, No. 1, July 1964, pp. 73–78.

Primary Examiner—Ronald L. Frinks
Attorney, Agent, or Firm—Howard R. Berkenstock, Jr.

[57] ABSTRACT

A chemically durable, biologically inert optical implant lens formed of a low density natural or synthetic crystal, such as Corundum, Sapphrie, Ruby, Sircon, Strontium Titanate, Diamond, Anatase or Ruby.

4 Claims, 2 Drawing Figures

ARTIFICIAL INTRAOCULAR LENS

BACKGROUND OF THE INVENTION

1. Field of the Invention

This invention relates to improvements in ophthalmology and more particularly to improvements in artificial intraocular lenses (pseudophakoi) used for the correction of aphakia and re-establishment of binocularity in aphakia.

2. Discussion of the Prior Art

Artificial intraocular lenses of various types have been used in the past and are being used at present. A summary of the history of such intraocular implants can be found in an article written by D. P. Choyce, published in the Annals of Ophthalmology, October, 1973, pages 1113–1120. In most cases lenses were made from organic high polymers such as, for example, polymethylmethacrylate. It has also been proposed to implant glass lenses and to utilize lenses made of pure silicate glass. Specific glass compositions have been proposed in the disclosure of U.S. Pat. No. 3,996,627, for example.

Although glasses have many advantages as ocular implants, some of which are explained in U.S. Pat. No. 3,996,627, they are, in most cases, of a density rendering finished lenses relatively high in weight and less than optimum in this respect as implants.

There being an ongoing need and search in the art for a desirable way to reduce the net weight of implantable lenses while maintaining maximum chemical stability and biological inertness, it is a principle object of this invention to afford a solution to the problem.

Other objects and advantages of the invention will become apparent from the following description.

SUMMARY OF THE INVENTION

According to the invention, intraocular implant lenses are formed of chemically stable and biologically inert natural or synthetic crystals having suitable refractive indices and relatively low density.

This use of natural crystals requires that their radioactivity is established to be below a tolerable level. In using synthetic crystals it is necessary to free all raw materials of traces of radioactive substances such as uranium or thorium. Special spectral transmittances desired for specific color vision effects and ultraviolet protection may be accomplished by incorporating rare earth or transition metal ions in the synthetic crystals.

Details of the invention will become more readily apparent from the following description when taken in conjunction with the accompanying drawings.

IN THE DRAWINGS

FIG. 1 is an illustration, in cross-section of an artificial intraocular lens in situ, the lens being exemplary of intraocular devices contemplated according to the invention; and FIG. 2 is an enlarged rear elevational view of the intraocular lens wherein its structure is illustrated in greater detail.

DESCRIPTION OF THE PREFERRED EMBODIMENTS

Artificial intraocular lenses (pseudophakoi) of various types and configurations, e.g. double convex and plano-convex in either one-piece or plural element structures have been used for the correction of aphakia and re-establishment of binocularity in aphakia. They are exemplary of intraocular implant devices to which crystals of the present invention are especially applicable and intended for use.

Figure 1:
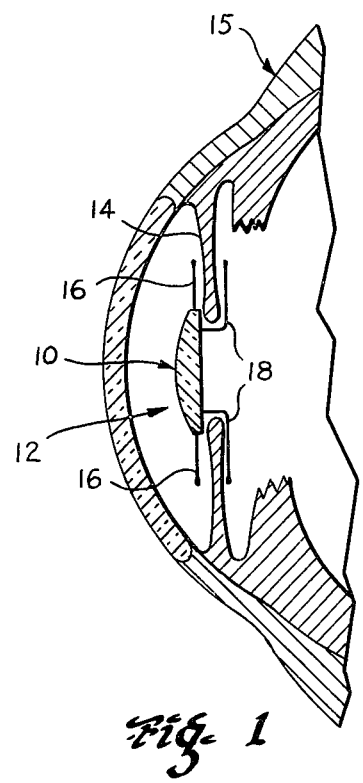
Figure 2:
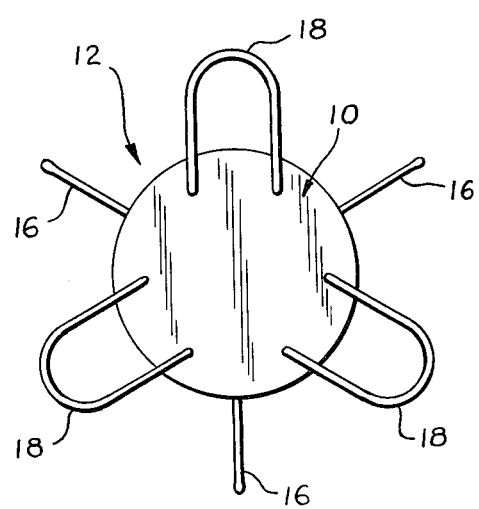

Iris-clip fixturing is usually used after intracapsular cataract extraction and iridocapsular fixturing is usually used after extracapsular extraction. The iris-clip lens may also be used following extracapsular surgery and, accordingly, has been depicted in FIG. 1 of the present drawings to illustrate a typical pseudophakos. It should be understood, however, that the present invention has similar applicability to all other types of pseudophakoi and that the presently illustrated arrangement for fixturing is purely illustrative and not limitative.

The present invention is directed more particularly to the lens element 10 of a pseudophakos 12 which is adapted to be fixtured to an iris 14 of an eye 15 with anterior and posterior clips 16 and 18 respectively. As it is well known in the art, the lens 10 may be plano-convex as illustrated or double convex and, in either case, provided with spherical, toric and/or aspherical surface curvatures.

The fixtures e.g. clips 16 and 18 may be formed of strands of plastic or wire and anchored in drilled or otherwise provided holes in lens 10 according to usual practice in such cases. For example, anchoring may be accomplished by cementing, interference fitting or shrink fitting. Further details of lens fixturing will not be discussed herein since the present invention is directed more particularly to an improvement in the lens per se, i.e. a lens material which is unique in the art both in its nature and characteristics of chemical stability with relatively low density.

The invention is accomplished by forming lens 10 of a natural or synthetic crystal having a refractive index, density and weight in air and in water which will afford a recipient the best possible duplication of function provided by healthy human crystalline lenses. In this respect, the use of any one of the hereinbelow listed crystals is contemplated.

| crystal | $n_o$ | $n_e$ | $\rho$ | $\alpha$ | $w_a$ | $w_i$ | color |
|---|---|---|---|---|---|---|---|
| Corundum | 1.768 | 1.759 | 3.99 | $15 \cdot 10^{-7}$ | 15.1 | 11.3 | clear |
| Sapphire | 1.768 | 1.759 | 3.99 | $15 \cdot 10^{-7}$ | 15.1 | 11.3 | bluish |
| Ruby | 1.768 | 1.759 | 3.99 | $15 \cdot 10^{-7}$ | 15.1 | 11.3 | red |
| Zircon | 1.90 | | 4.70 | $30 \cdot 10^{-7}$ | 16.2 | 12.8 | clear-yellow |
| Strontium Titanate (SrTiO$_3$) | 2.408 | | 5.10 | — | 15.0 | 12.1 | clear |
| Diamond | 2.417 | | 3.52 | $13 \cdot 10^{-7}$ | 10.3 | 7.4 | clear |
| Anatase | 2.534 | 2.493 | 3.90 | — | 11.2 | 8.3 | clear |

-continued

| crystal | $n_o$ | $n_e$ | $\rho$ | $\alpha$ | $w_a$ | $w_i$ | color |
|---|---|---|---|---|---|---|---|
| Rutile | 2.616 | 2.903 | 4.24 | $71 \cdot 10^{-7}$ | 12.0 | 9.2 | clear |

$n_o$ = refractive index for ordinary ray;
$n_e$ = refractive index for extraordinary ray;
$\rho$ = density in g/cm$^3$;
$\alpha$ = coefficient of thermal expansion ($°$ C)$^{-1}$;
$w_a$ = weight (in mg) in air of a plano-convex lens of edge thickness 0.12 mm, diameter 5.0 mm, (power 20 m$^{-1}$ when immersed in medium of 1.335 index).
$w_i$ = weight of same lens in water From the foregoing, it can be seen that highly desirable crystal is the diamond which has the least density and weight in water of the listing. In connection with crystals which exhibit birefringence, this may be compensated for by choosing a proper orientation of optical axes. It is also pointed out that the achievement of a spectral transmittance desired for specific color vision effects and/or ultraviolet protection may be accomplished by incorporating, in conventional fashion, rare earth or transition metal ions in the manufacture of synthetic crystals during crystal growth. Synthetic crystal growing techniques including the incorporation of rare earth or other metal ions with basic raw materials are well known to the artisan and, accordingly, will not be detailed herein.

Those skilled in the art will also readily appreciate that there are various other modifications and adaptations of the precise form of pseudophakos here shown. For example, compensation for birefringence may be accomplished with an incorporation of combinations of lens configurations and/or multiple lens components. Accordingly, the foregoing illustrations are not to be interpreted as restrictive of the invention beyond that necessitated by the following claims.

We claim:

1. An ocular implant lens having optically finished front and rear surfaces, center thickness and index of refraction together affording an ophthalmic power suitable for intraocular use and wherein said lens is formed of a crystalline material selected from the group consisting of Corundum, Sapphire, Ruby, Zircon, Strontium Titanate, Diamond, Anatase and Rutile.

2. A lens according to claim 1 including intraocular fixturing means.

3. A lens according to claim 2 wherein said fixturing means comprises iris clips.

4. A lens according to claim 2 wherein said fixturing comprises iridocapsular loops.

* * * * *